United States Patent [19]

Schönafinger et al.

[11] Patent Number: 4,681,891

[45] Date of Patent: Jul. 21, 1987

[54] DIHYDRO-2,6-DIMETHYL PYRIDINES, FORMULATIONS AND METHOD OF USE FOR TREATING ANGINA PECTORIS, HIGH BLOOD PRESSURE OR DISTURBANCES OF CEREBRAL OR PERIPHERAL BLOOD FLOW

[75] Inventors: Karl Schönafinger, Alzenau; Helmut Bohn, Schöneck; Piero Martorana, Bad Homburg; Rolf-Eberhard Nitz, Frankfurt, all of Fed. Rep. of Germany

[73] Assignee: Cassella Aktiengesellschaft, Fed. Rep. of Germany

[21] Appl. No.: 796,806

[22] Filed: Nov. 12, 1985

[30] Foreign Application Priority Data

Nov. 27, 1984 [DE] Fed. Rep. of Germany ....... 3443179

[51] Int. Cl.⁴ ................. C07D 413/04; C07D 417/04; A61K 31/44
[52] U.S. Cl. .................... 514/340; 546/277; 546/280; 546/284; 546/256; 546/251; 514/342
[58] Field of Search .................. 546/277; 514/340

[56] References Cited

U.S. PATENT DOCUMENTS

| | | | |
|---|---|---|---|
| 4,144,343 | 3/1979 | Baldwin | 514/340 |
| 4,145,432 | 3/1979 | Sato | 546/277 |
| 4,260,765 | 4/1981 | Harrison | 546/280 |
| 4,414,213 | 11/1983 | Poindexter | 514/210 |
| 4,558,058 | 12/1985 | Schonafinger et al. | 514/342 |

Primary Examiner—Alan L. Rotman
Attorney, Agent, or Firm—Thomas L. Tully

[57] ABSTRACT 1,4-dihydropyridines of the formula I

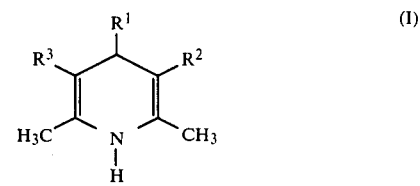

wherein $R^1$ denotes optionally substituted phenyl, pyridyl or thienyl, $R^2$ denotes optionally substituted oxadiazolyl, thiadiazolyl or thiazolyl and $R^3$ denotes hydrogen or —COOH, their preparation by a modified Hantzsch synthesis and their use as a calcium-agonist in pharmacy.

8 Claims, No Drawings

DIHYDRO-2,6-DIMETHYL PYRIDINES, FORMULATIONS AND METHOD OF USE FOR TREATING ANGINA PECTORIS, HIGH BLOOD PRESSURE OR DISTURBANCES OF CEREBRAL OR PERIPHERAL BLOOD FLOW

The invention relates to 1,4-dihydropyridines of the formula I

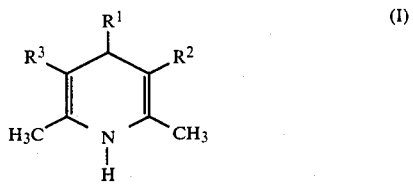

wherein $R^1$ denotes phenyl, pyridyl or thienyl, $R^2$ denotes oxadiazolyl, thiadiazolyl or thiazolyl and $R^3$ denotes hydrogen or —COOH, and a phenyl, pyridyl or thienyl radical represented by $R^1$ is unsubstituted or contains one or two identical or different substituents from the group comprising alkyl having 1 to 4 C atoms, alkoxy having 1 to 4 C atoms, halogen, trifluoromethyl, nitro, cyano or benzyloxy, and an oxidiazolyl, thiadiazolyl or thiazolyl radical represented by $R^2$ is unsubstituted or contains a substituent, or, in the case of thiazolyl, contains one or two identical or different substituents, from the group comprising alkyl having 1 to 4 C atoms, alkoxy having 1 to 4 C atoms, alkylthio having 1 to 4 C atoms, aralkyl having 7 to 9 C atoms, alkoxyalkyl having a total of 2 to 5 C atoms, cycloalkyl having 5 to 6 C atoms, aminocarbonylmethylthio, methoxycarbonyl, ethoxycarbonyl or phenyl, to salts thereof with pharmacologically acceptable acids and to the preparation of these compounds and their use as medicaments.

Pyridyl radicals represented by $R^1$ are pyrid-2-yl, pyrid-3-yl and pyrid-4-yl; thienyl radicals represented by $R^2$ are thien-2-yl or thien-3-yl. Of the thiazolyl, thiadiazolyl and oxadiazolyl radicals represented by $R^2$, 1,3-thiazol-2-yl, 1,2,4-thiadiazol-5-yl, 1,3,4-thiadiazol-2-yl, 1,2,4-oxadiazol-5-yl and 1,2,4-oxadiazol-2-yl are preferred.

Substituted phenyl radicals represented by $R^1$ are substituted in the 2-, 3- or 4-position, preferably in the 2-position or 3-position, or in the 2-position and the 3-position.

Alkyl radicals and alkoxy radicals which are optionally attached as substituents to a phenyl radical or heterocyclic radical represented by $R^1$ and $R^2$ can be linear or branched. Examples of such radicals are methyl, ethyl, prop-1-yl, prop-2-yl, n-but-1-yl, n-but-2-yl, 2-methylprop-1-yl, tert.-butyl, methoxy, ethoxy, prop-1-oxy, prop-2-oxy, n-butoxy, but-2-oxy, 2-methylprop-1-oxy and tert.-butoxy.

Alkyl and alkoxy radicals having 1 or 2 C atoms, in particular methyl and methoxy, are preferred.

An alkylthio radical in the position of a substituent of a heterocyclic radical represented by $R^2$ can also be linear or branched. Examples of such alkylthio radicals are methylthio, ethylthio, prop-1-ylthio, prop-2-ylthio, n-but-1-ylthio, but-2-yl-thio, 2-methylprop-1-ylthio and tert.-butylthio. Alkylthio radicals having 1 to 2 C atoms are preferred, especially methylthio. Aralkyl radicals which, in a given case, are substituents of a heterocyclic radical represented by $R^2$ are, in particular, phenalkyl radicals having 1 to 3 C atoms in the alkyl bridge, such as benzyl, phenethyl, 3-phenylprop-1-yl, 2-phenylprop-1-yl, 1-phenylprop-2-yl and 2-phenylprop-2-yl. Benzyl and phenethyl are preferred phenalkyl radicals.

The carbon chains of alkoxyalkyl radicals which, in a given case, are substituents of a heterocyclic radical represented by $R^2$ can also be linear or branched. Examples of such alkoxyalkyl radicals are methoxymethyl, ethoxymethyl, prop-1-oxymethyl, prop-2-oxymethyl, n-butoxymethyl, sec.-butoxymethyl, isobutoxymethyl, tert.-butoxymethyl, methoxyethyl, ethoxyethyl, propoxyethyl, isopropoxyethyl, 1-methoxyprop-2-yl, 1-methoxyprop-3-yl, 2-methoxyprop-1-yl, the corresponding isomeric ethoxypropyl radicals and the 12 isomeric methoxybutyl radicals.

Alkoxyalkyl radicals which contain unbranched carbon chains or carbon chains attached via primary C atoms are preferred.

Of the cycloalkyl radicals mentioned as possible substituents of a heterocyclic radical represented by $R^2$, the cyclohexyl radical is preferred.

Halogen atoms which, in a given case, are substituents of a phenyl radical represented by $R^1$ are preferably fluorine, chlorine or bromine, especially chlorine or bromine; the particularly preferred halogen is chlorine.

Thus a preferred meaning of $R^1$ is phenyl which is unsubstituted or which contains one or two identical or different substituents from the series comprising halogen, methyl, methoxy, nitro, trifluoromethyl, cyano or benzyloxy.

The following are examples of a substituted phenyl radical represented by $R^1$: 2-chlorophenyl, 3-chlorophenyl, 4-chlorophenyl, 2,3-dichlorophenyl, 2-nitrophenyl, 3-nitrophenyl, 3-cyanophenyl, 3-methoxyphenyl, 3-trifluoromethylphenyl, 2-trifluoromethylphenyl, o-tolyl, m-tolyl or p-tolyl. Particularly preferentially $R^1$ denotes a phenyl group which is monosubstituted by cyano, nitro or chlorine or which is disubstituted by chlorine, the substituents preferably being present in the 2-position and/or 3-position of the phenyl nucleus. Very particularly preferentially $R^1$ denotes 2-nitrophenyl, 3-nitrophenyl, 3-cyanophenyl, 2-chlorophenyl and 2,3-dichlorophenyl.

Substituents which are particularly preferred for a heterocyclic radical represented by $R^2$, especially for a 1,2,4-oxadiazolyl or 1,3,4-oxadiazolyl radical, are: methyl, ethyl, isopropyl and benzyl. 1,3,4-Oxadiazol-2-yl, 5-methyl-1,3,4-oxadiazol-2-yl, 5-ethyl-1,3,4-oxadiazol-2-yl, 3-methyl-1,2,4-oxadiazol-5-yl, 3-ethyl-1,2,4-oxadiazol-5-yl and 3-benzyl-1,2,4-oxadiazol-5-yl are particularly preferred for $R^2$. The preparation of the compounds, according to the invention, of the formula I is effected by analogous processes which constitute variants of the known Hantzsch synthesis. The most expedient route of synthesis for building up the dihydropyridine system is the condensation of 1 mole of a readily hyrolysable 3-aminocrotonic acid ester, preferably β-cyanoethyl 3-aminocrotonate (formula IIa) with 1 mole of an ylidene compound, the α,β-unsaturated ketone of the formula III:

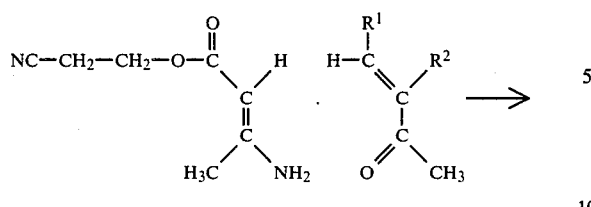

(IIa)         (III)

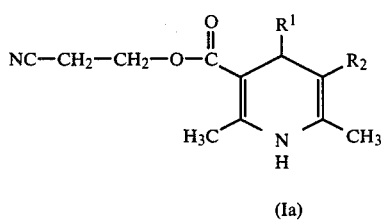

(Ia)

After the synthesis of the dihydropyridinecarboxylic acid ester of the formula Ia, the ester group is saponified in a manner which is in itself known in an aqueous medium in the presence of an acid or, preferably, a base. The compounds, according to the invention, of the formula I in which $R^3$ is the carboxyl group (—COOH) or a salt thereof are then obtained in this manner.

If compounds of the formula I in which $R^3$ is hydrogen are to be prepared, the corresponding compounds in which $R^3$ denotes the carboxyl group are decarboxylated in a manner which is in itself known.

The present invention also relates, therefore, to a process for the preparation of the 1,4-dihydropyridines of the formula I

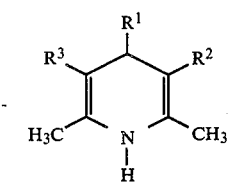          (I)

wherein $R^1$, $R^2$ and $R^3$ have the meanings indicated above, which is characterised in that an aminocrotonic acid ester of the formula II

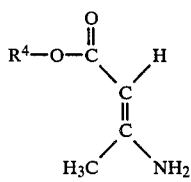

wherein $R^4$ is the radical of an alcohol which can readily be split off by hydrolysis is reacted, in an inert organic solvent at a temperature between 10° C. and the boiling point of the solvent employed, with an α,β-unsaturated ketone of the formula III

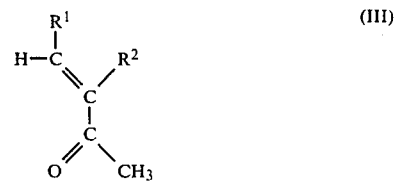  (III)

to give a 1,4-dihydropyridinecarboxylic acid ester of the formula Ia

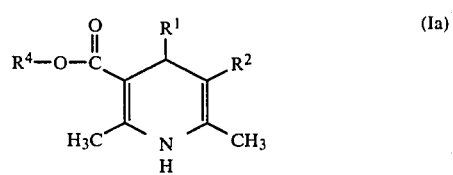  (Ia)

wherein $R^1$ to $R^4$ have the meanings mentioned above, this ester is then hydrolysed in an aqueous medium in the presence of an acid or a base to give a compound of the formula I in which $R^3$ is the carboxyl group, and, if desired, the resulting compound is decarboxylated in a manner which is in itself known and, if appropriate, is reacted with a pharmacologically acceptable acid to give the corresponding acid addition salt.

Radicals $R^4$ which can be split off readily by hydrolysis are derived from alcohols which carry an electron-attracting substituent in conjugation with or in a position adjacent to the hydroxyl group. Examples of electron-attracting substituents are, for example, the carbonyl group, the sulphonyl group, the sulphoxide group, carboxylic or sulphonic ester groups, the nitro group and the cyano group. The β-cyanoethyl radical is particularly preferred for $R^4$.

3-Aminocrotonic acid esters of the formula II are known compounds. They can be prepared readily by reacting the corresponding acetoacetic ester with ammonia. -Cyano-ethyl 3-aminocrotonate, which is particularly preferred, can also be prepared readily in an analogous manner, for example in accordance with the instructions in German Offenlegungsschrift 2,117,571 and German Offenlegungsschrift 2,117,572.

Insofar as they are not already known, the ylidene compounds of the formula III required as starting components are prepared by the method of Organic Reactions XV, 204 et seq., (1967). The following are examples of suitable starting compounds of the formula III: 1-(2,3-dichlorophenyl)-2-(1,3,4-oxadiazol-2-yl)-1-buten-3-one, 1-(3-nitrophenyl)-2-(1,3,4-oxadiazol-2-yl)-1-buten-3-one, 1-(2-nitrophenyl)-2-(1,3,4-oxadiazol-2-yl)-1-buten-3-one, 1-(2-chlorophenyl)-2-(1,3,4-oxadiazol-2-yl)1-buten-3-one, 1-(3-cyanophenyl)-2-(1,3,4-oxadiazol-2-yl)-1-buten-3-one, 1-pyridin-3-yl)-2-(1,3,4-oxadiazol-2-yl)-1-buten-3-one, 1-(thien-2-yl)-2-(1,3,4-oxadiazol-2-yl)-1-buten-3-one, 1-(3-trifluoromethylphenyl)-2-(1,3,4-oxadiazol-2-yl)-1-buten-3-one, 1-(2,3-dichlorophenyl)2-(2-methyl-1,3,4-oxadiazol-5-yl)-1-buten-3-one, 1-(2,3-dichlorophenyl)-2-(2-benzyl-1,3,4-oxadiazol-5-yl)-1-buten-3-one, 1-(2-methylphenyl)-2-(3-ethyl-1,2,4-oxadiazol-5-yl)-1-buten-3-one, 1-(3-methoxyphenyl)-2-(3-tert.-butyl-1,3,4-oxadiazol-5-yl)-1-buten-3-one, 1-(3-chlorophenyl)-2-(1,2,4-thiadiazol-5-yl)-1-buten-3-one, 1-(2-trifluoromethyl)-2-(3-benzyl-1,2,4-oxadiazol-5-yl)-1-buten-3-one, 1-(2,5-dichlorophenyl)-2-(3-methylthio-1,3,4-oxadiazol)-1-buten-3-one, 1-(pyridin-2-yl)-2-(4- methyl-5-ethoxycarbonylthiazol-2-yl)-1-buten-3-one, 1-(3-nitrophenyl)-2-(3-methyl-1,2,4-oxadiazol-5-yl)-1-buten-3-one and 1-(2,3-dichlorophenyl)-2-(3-ethyl-1,2,4-oxadiazol-5-yl)-1-buten-3-one.

A particularly expedient embodiment of this process of preparation consists in combining the condensation reaction of the aminocrotonic acid ester with the ylidene compound in a one-pot process together with the synthesis of the ylidene compound.

In this process, the ylidene compound is obtained by subjecting a aldehyde of the formula IV to a condensation reaction with a ketone of the formula V. In this process variant, therefore, 1 mole of the readily hydrolysable 3-aminocrotonic acid ester is reacted with 1 mole of an aldehyde of the formula IV and 1 mole of a ketone of the formula V, in order to build up the dihydropyridine skeleton.

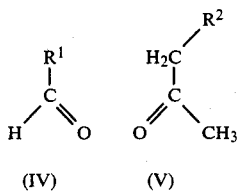

(IV)   (V)

It will be evident to those skilled in the art that, in the condensation reaction of the aminocrotonic acid ester of the formula II with the unsaturated ketone of the formula III or with the aldehyde of the formula IV and the ketone of the formula V, one or other component can be employed in an excess of up to 100%, preferably up to 20%, if this appears expedient in the interests of complete reaction of one of the components, for example of a component which is difficult of access and therefore correspondingly expensive, or if the component employed in excess can be separated from the end product particularly readily. It is also known to those skilled in the art that the use of an excess of one of the components results in an increase in the reaction rate under otherwise constant reaction conditions, or permits the reaction to be carried out under milder conditions.

If they are not already known, the aldehydes of the formula IV used as the starting components in this process variant can, for example, be prepared by the method described by E. Mosettig, Organic Reactions VIII, 218 et seq., (1954). The following are examples of suitable aldehydes of the formula IV: benzaldehyde, 2-, 3- or 4-methylbenzaldehyde, 2-, 3- or 4-ethylbenzaldehyde, 2-, 3- or 4-isopropylbenzaldehyde, 2-, 3- or 4-tert.-butylbenzaldehyde, 2-, 3- or 4-methoxybenzaldehyde, 2-, 3- or 4-isopropoxybenzaldehyde, 2-, 3- or 4-bromobenzaldehyde, 2-, 3- or 4-chlorobenzaldehyde, 2-, 3- or 4-fluorobenzaldehyde, 2-, 3- or 4-cyanobenzaldehyde, 2-, 3- or 4-trifluoromethylbenzaldehyde, 2-, 3- or 4-nitro-benzaldehyde, 2,4-dimethylbenzaldehyde, 2,6-dimethylbenzaldehyde, 2,4-dichlorobenzaldehyde, 2,6-dichlorobenzaldehyde, 2,4-dibromobenzaldehyde, 2,6-dibromobenzaldehyde 2,4-dinitrobenzaldehyde, 2,6-dinitrobenzaldehyde, 2,4-diethylbenzaldehyde, 2,6-diethylbenz-aldehyde, 3-chloro-4-trifluoromethylbenzaldehyde, 3-methyl-4-tri-fluoromethylbenzaldehyde, 3-methoxy-4-chlorobenzaldehyde, 2-methyl-4-cyanobenzaldehyde, pyridine-2-aldehyde, pyridine-3-aldehyde, pyridine-4-aldehyde, 4-methylpyridine-2-aldehyde, 5-methylpyridine-2-aldehyde, 6-methylpyridine-2-aldehyde, thiophene-2-aldehyde, thiophene-3-aldehyde, 5-nitrothiophene-2-aldehyde, 5-methylthiophene-2-aldehyde, 5-chlorothiophene-2-aldehyde and 5-methoxythiophene-2-aldehyde.

Insofar as they are not already known, the ketones of the formula V can be prepared by the process described in Monatshefte für Chemie 113, 781 et seq. (1982). The following are examples of suitable starting compounds of the formula V: 5-acetonyl-1,2,4-oxadiazole, 3-methyl-5-acetyl-1,2,4-oxadiazole, 3-ethyl-5-acetyl-1,2,4-oxadiazole, 3-tert.-butyl-5-acetyl-1,2,4-oxadiazole, 3-methylthio-5-acetyl-1,2,4-oxadiazole, 3-benzyl-5-acetyl-1,2,4-oxadiazole, 2-acetonyl-1,3,4-oxadiazole, 5-methyl-2-acetonyl-1,3,4-oxa-diazole, 5-isopropyl-2-acetonyl-1,3,4-oxadiazole, 3-acetonyl-1,2,4-oxadiazole, 5-ethyl-3-acetonyl-1,2,4-oxadiazole, 5-ethylthio-3-acetonyl-1,2,4-oxadiazole, 5-phenethyl-3-acetonyl-1,2,3-oxadiazole, 5-acetonyl-1,2,3-thiadiazole, 3-ethyl-5-acetonyl-1,2,4-thiadiazole and 3-benzyl-5-acetonyl-1,2,4-thiadiazole.

The building up of the dihydropyridine skeleton by the two process variants indicated is carried out at room temperature (20° C.) or, especially, at an elevated temperature, for example within a range from 20° to 120° C. In the case of both variants the reaction is preferably carried out within the temperature range from 40° to 100° C., especially at the reflux temperature of the solvent or solvent mixture used. The reaction is normally carried out under normal pressure, but it can also be carried out under a pressure differing from normal pressure.

The reactions are carried out in water and an inert organic solvent. Examples of suitable solvents are alcohols, in particular those having 1 to 6 C atoms, such as, for example, methanol, ethanol, isopropanol, n-propanol, isobutanol, sec.-butanol and tert.-butanol, n-, iso-, sec.- or tert.-pentanol, n-hexanol, cyclopentanol or cyclohexanol; ethers, in particular those having 2 to 8 C atoms in the molecule, such as, for example, diethyl ether, methyl ethyl ether, di-n-propyl ether, diisopropyl ether, methyl n-butyl ether, ethyl propyl ether, dibutyl ether or tetrahydrofuran; 1,4-dioxane, 1,2-dimethoxyethane or bis-β-methoxyethyl ether; polyethers, such as, for example, polyethylene glycols having a molecular weight of up to approx. 600; oligoethylene glycol dimethyl ethers, such as, for example, pentaglyme; glycols and par-tially etherified glycols, such as, for example, ethylene glycol, propylene glycol, trimethylene glycol, ethylene glycol monomethyl ether, ethylene glycol monoethyl ether or diethylene glycol monoethyl ether; ketones, in particular those having 3 to 10 C atoms in the molecule, such as, for example, acetone, methyl ethyl ketone, methyl n-propyl ketone, diethyl ketone, 2-hexanone, 3-hexanone, di-n-propyl ketone, diisopropyl ketone, diisobutyl ketone, cyclopentanone, cyclohexanone, cyclohexanone, benzophenone or acetophenone; aliphatic hydrocarbons, such as, for example, low-boiling and high-boiling grades of petroleum ether; aromatic hydrocarbons, such as, for example, benzene, toluene, o-, m- and p-xylene or pyridine; halogenated aliphatic or aromatic hydrocarbons, such as, for example methylene chloride, chloroform, carbon tetrachloride, ethylene chloride, chlorobenzene or dichlorobenzene; nitriles, such as, for example, acetonitrile; amides, such as, for example, dimethylformamide or N-methylpyrrolidone; hexamethylphosphoric acid triamide; sulphoxides, such as, for example, dimethyl sulphoxide; or water. It is also possible to use mixtures of different solvents. As a rule, alcohols or mixtures of alcohols and water are preferred.

As already stated above, the saponification of the esters of the formula Ia can be effected by hydrolysis in the presence of acids or bases. The use of bases is preferred. Suitable bases are primarily inorganic bases, preferably alkali metal hydroxides, such as sodium hydroxide or potassium hydroxide. The bases can be employed in molar amounts or in a 2-fold to 4-fold excess.

Water has proved advantageous as the reaction medium. In order to carry out the reaction in a homogeneous manner, it is expedient, as a rule, to add an inert, water-miscible organic solvent. Solvents of this type include alcohols, such as methanol, ethanol, propanol, isopropanol or 2-methoxyethanol, ethers, such as dioxane, tetrahydrofuran or 1,2-dimethoxyethane, or pyridine, dimethylformamide or dimethyl sulphoxide.

The use of methanol, ethanol, 2-methoxyethanol and 1,2-dimethoxyethane is particularly advantageous. In the reaction temperatures are between 0° and 100° C., in particular between 20° and 50° C. and preferably at room temperature. When the hydrolysis is carried out, the compounds (I) are produced in the reaction mixture in the form of salts. It is therefore expedient to dilute the mixture with water and to extract it by shaking with methylene chloride. The aqueous phase is then acidified, whereupon the compounds, according to the invention, of the formula I in which $R^3$ is the carboxyl group are, as a rule, precipitated and can be removed by filtration. The possibly desirable decarboxylation of these compounds to give the compounds, according to the invention, of the formula I in which $R^3$ is hydrogen is carried out, as a rule, at 100° to 200° C., and it has proved expedient to carry out the reaction in an inert solvent which boils within this temperature range. Examples of solvents of this type are toluene, xylene, chlorobenzene, dichlorobenzene, nitrobenzene, glycol, methoxyethanol, diethylene glycol, 2-ethoxyethanol, propanediol or dimethyl sulphoxide; diethylene glycol and temperatures from 160° to 180° C. are particularly preferred.

If they possess basic substituents, the 1,4-dihydropyridine derivatives, according to the invention, of the formula I form acid addition salts with inorganic or organic acids. The following are examples of suitable acids: hydrogen chloride, hydrogen bromide, naphthalenedisulphonic acids, in particular naphthalene-1,5-disulphonic acid, or phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. Pharmacologically acceptable acid addition salts are preferred. The acid addition salts are prepared in the customary manner by combining the components, expediently in a suitable solvent or diluent. In the synthesis of the compounds of the formula I, the acid addition salts can be produced initially in the course of working-up. The free compounds of the general formula I can, if desired, be obtained from the acid addition salts in a known manner, for example by dissolving or suspending the latter in water and rendering the mixture alkaline, for example with sodium hydroxide solution, and subsequently isolating the product.

The compounds, according to the invention, of the formula (I) possess an asymmetric carbon atom in the 4-position of the dihydropyridine ring. These compounds therefore occur in the form of racemates and in the form of optically active enantiomers. In the event that the compounds of the formula I possess more than one asymmetric atom, diastereomers and mixtures thereof are also found. Mixtures of diastereomers and racemic mixtures of enantiomers can be separated into the individual components by known processes. Mixtures of diastereomers can, for example, be separated into the diastereomers by fractional recrystallisation or by means of chromatographic processes. A racemate can, for example, be converted by reaction with a suitable enantiomeric compound into a mixture of a diastereomeric salts which is then separated into the individual diastereomeric salts, for example by fractional recrystallisation. The diastereomeric salts are then converted into the enantiomeric compounds in a known manner.

It is already known that certain 1,4-dihydropyridines have interesting pharmacological properties (F. Bossert, W. Vater "Die Naturwissenschaften" 57, 578, (1971). As a rule, the known active compounds are 1,4-dihydropyridine-3,5-dicarboxylic acid esters.

It is also already known that 1,4-dihydropyridines possess vasodilative properties and can be used as coronary agents and antihypertensive agents (cf. for example, German Offenlegungs-schrift 2,629,892 and German Offenlegungsschrift 2,752,820). This action of the 1,4-dihydropyridines is based on a calcium-antagonistic action (cf. A. Fleckenstein, Ann. Rev. Pharmacol. Toxicol. 17, 149 to 166 (1977)).

A calcium-antagonistic action of 5-oxadiazolyl-, 5-thiazolyl- and 5-thiadiazolyl-dihydropyridine-3-carboxylic acid esters has also been disclosed (see U.S. Pat. No. 4,558,058). In contrast with this, it is known from EP-A-71,819 that a dihydro-pyridine derivatives of the general formula A

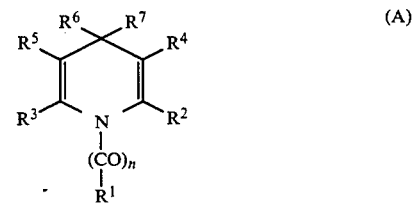

in which the symbols $R^1$ to $R^7$ have wide ranges of definition exhibit a positive inotropic action.

The compounds of the formula I of the present invention exhibit a pronounced calcium-agonistic action and are considerably superior to the compounds disclosed in EP-A-71,819 in respect of duration of action.

The compounds of the formula I and their pharmacologically acceptable acid addition salts can, therefore, be administered with particular advantage to humans as medicaments on their own, in mixtures with one another or in the form of pharmaceutical formulations which permit enteral or parenteral administration and which contain, as the active ingredient, an effective dose of at least one compound of the formula I or of an acid addition salt thereof together with customary pharmaceutically acceptable excipients and additives. The formulations normally contain about 0.5 to 90% by weight of the therapeutically active compound.

The medicaments can be administered orally, for example in the form of pills, tablets, lacquered tablets, coated tablets, granules, hard and soft gelatine capsules, solutions, syrups, emulsions or suspensions or aerosol mixtures. Administration can, however, also be effected rectally, for example in the form of suppositories, or parenterally, for example in the form of injection solutions, or percutaneously, for example in the form of ointments or tinctures.

The preparation of the pharmaceutical formulations is effected in a manner which is in itself known, using pharmaceutically inert inorganic or organic excipients. For the preparation of pills, tablets, coated tablets and hard gelatine capsules it is possible to use, for example, lactose, maize starch or derivatives thereof, talc, stearic acid or salts thereof etc. Examples of excipients for soft gelatine capsules and suppositories are fats, waxes, semisolid and liquid polyols, natural or hardened oils etc. Examples of suitable excipients for the preparation of solutions and syrups are water, sucrose, invert sugar, glucose, polyols etc. Examples of suitable excipients for the preparation of injection solutions are water, alcohols, glycerol, polyols, vegetable oils etc.

In addition to the active compounds and excipients, the pharmaceutical formulations can also contain additives, such as, for example, fillers, extenders, distintegrators, binders, lubricants, wetting agents, stabilisers, emulsifiers, preservatives, sweeteners, colorants, flavouring or aromatising agents, thickeners, diluents and buffer substances and also solvents or solubilisers or agents for achieving a depot effect as well as salts for altering the osmotic pressure, coating agents or antioxidants. They can also contain two or more compounds of the formula I and/or pharmacologically acceptable acid addition salts thereof and also other therapeutically active substances.

The following are examples of other therapeutically active substances of this type: β-receptor blockers, such as, for example, propranolol, pindolol or metoprolol; antianginal agents, such as, for example, carbochromen or molmoldomine; tranquilisers, such as, for example, barbiturate acid derivates, 1,4-benzodiazepins and meprobamate; diuretics, such as, for example, chlorothiazide; agents for tonicising the heart, such as, for example, digitalis formulations, hypotensive agents, such as, for example, hydralazine, dihydralazine and prazosin; clonidine and rauwolfia alkaloids; agents which lower the fatty acid level in the blood, such as, for example, bezafibrate and fenofibrate; and agents for the prophylaxis of thromboses, such as, for example, phenprocoumon.

The dosage can vary within wide limits and should be adjusted to suit the individual factors in each individual case. In general, a daily dose of about 0.01 to 10 mg/kg, preferably 0.05 to 5 mg/kg, of body weight is appropriate for achieving effective results in the case of oral administration. In the case of intravenous administration, the daily dose is generally about 0.001 to 10 mg/kg, preferably 0.01 to 5 mg/kg, of body weight. The daily dose is normally subdivided into several, for example 2, 3 or 4, partial administrations, particulary when fairly large amounts are administered. Depending on individual behaviour, it can, in a given case, become necessary to deviate upwards or downwards from the daily dose indicated.

To demonstrate the hemodynamic action of the compounds according to the invention, studies were carried out in the mongrel dog under pentobarbital anaesthetic (30 to 40 mg/kg intravenously). Respiration was effected with a Bird Mark 7 respirator. The end expiratory carbon dioxide content (measured with an ultrared absorption recorder) was between 4.5 and 5% by volume. Throughout the entire experiment continuous intravenous infusion with pentobarbital=5 mg (in 6 ml)/kg/h was administered through the cephalic vein, in order to ensure a constant level of anaesthesia. Before the actual experiment a period of about 1 hour was allowed for all the hemodynamic parameters to become established (steady state). The actual experiment was then started.

The systolic and diastolic blood pressure were measured peripherally in the femoral artery via a Statham pressure recorder.

The results obtained are indicated in the table below:

| Blood Pressure | Preparation 1 0.1 mg/kg intravenously | Preparation 2 0.1 mg/kg intravenously |
|---|---|---|
| systolic | | |
| 1. before administration, mmHg | 130 | 115 |
| 2. after administration, mmHg | 340 | 270 |
| 3. difference 2 − 1, mmHg | 210 | 155 |
| 4. duration of action, min | 10 | 5 |
| diastolic | | |
| 1. before administration, mmHg | 95 | 75 |
| 2. after administration, mmHg | 180 | 200 |
| 3. difference 2 − 1, mmHg | 85 | 125 |
| 4. duration of action, min | 10 | 5 |

Preparation 1=1,4-dihydro-2,6-dimethyl-3-(1,3,4-oxadiazol-2-yl)-4-(2-chlorophenyl)-pyridine (according to example 3 below)

Preparation 2=1,4-dihydro-2,6-dimethyl-3-nitro-4-(2-trifluoromethyl-phenyl)-pyridine-3-carboxylic acid methyl ester (reference substance).

The present invention is further illustrated by the following illustrative embodiments.

EXAMPLE 1

1,4-Dihydro-2,6-dimethyl-4-(2-chlorophenyl)-5-(1,3,4-oxadiazol-2-yl)-pyridine-3-carboxylic acid 18.9 g of (1,3-oxadiazol-2-yl)-acetone, 23 g of cyanoethyl aminocrotonate and 20 g of 2-chlorobenzaldehyde in 100 ml of isopropanol are boiled under reflux for 8 hours. The mixture is then stirred overnight at room temperature and for 5 hours at 0° C. The precipitate which has been deposited is filtered off with suction and recrystallised from ether/petroleum ether: yield 24 g (44.7% of theory) of 2-cyanoethyl 1,4-dihydro-2,6-dimethyl-4-(2-chlorophenyl)-5-(1,3,4-oxadiazol-2-yl)-pyridine-3-carboxylate of melting point 180° to 182° C.

14 g of the 2-cyanoethyl 1,4-dihydro-2,6-dimethyl-4-2(chlorophenyl)-5-(1,3,4-oxadizaol-2-yl)-ryridine-3-carboxylate thus prepared are stirred in a solution of 4.8 g of NaOH in 120 ml of water and 60 ml of dimethoxyethane for 3 hours at room temperature. The mixture is diluted with 100 ml of water and is extracted by shaking with three times 50 ml of $CH_2Cl_2$. The water phase is acidified by adding concentrated hydrochloric acid. The precipitate which has been deposited is then filtered off with suction, washed with water until it is neutral and dried in vacuo at 50° C. This gives 11.2 g (corresponding to 92.8% of theory) of 1,4-dihydro-2,6-dimethyl-4-(2-chlorophenyl)-5-(1,3,4-oxadiazol-2-yl)-pyridine-3-carboxylic acid of melting point 187°–190° C.

| Analysis: $C_{16}H_{13}N_3O_3Cl$ (molecular weight 330.8) | | | | | | | | | | |
|---|---|---|---|---|---|---|---|---|---|---|
| Calculated: | C: | 58.09 | H: | 3.96 | N: | 12.70 | O: | 14.51 | Cl: | 10.73 |
| Found: | | 58.2 | | 4.0 | | 12.5 | | 14.3 | | 10.8 |

EXAMPLE 2

1,4-Dihydro-2,6-dimethyl-4-(2,3-dichlorophenyl)-5-(1,3,4-oxadiazol-2-yl)-pyridine-3-carboxylic acid 28.3 g of 1-(2,3-dichlorophenyl)-2-(1,3,4-oxadiazol-2-yl)-but-1-en-3-one and 15.4 g of 2-cyanoethyl aminocrotonate in 100 ml of DMF are heated at 80° C. for 10 hours. The cooled reaction mixture is poured into 400 ml of water and extracted by shaking with twice 100 ml of ethyl acetate. The organic phase is dried over $Na_2SO_4$ and concentrated. The residue is recrystallised from isopropanol: 33 g (~72.7% of theory) of 2-cyanoethyl 1,4-dihydro-2,6-dimethyl-4-(2,3-dichlorophenyl)-5-(1,3,4-oxadiazol-2-yl)-pyridine-3-carboxylate of melting point 210° to 212° C.

30 g of the 2-cyanoethyl 1,4-dihydro-2,6-dimethyl-4-(2,3-dichlorophenyl)-5-(1,3,4-oxadiazol-2-yl)-pyridine-3-carboxylate thus prepared are stirred in a solution of 8.7 g of NaOH in 220 ml of water and 110 ml of dimethoxyethane for 3 hours at room temperature. The mixture is diluted with 200 ml of water and is extracted by shaking with three times 100 ml of $CH_2Cl_2$. The water phase is acidified by adding concentrated hydrochloric acid. The precipitate which has been deposited is then filtered off with suction, washed with water until it is neutral and dried in vacuo at 50° C. This gives 22.0 g (corresponding to 91.1% of theory) of 1,4-dihydro-2,6-dimethyl-4-(2,3-dichlorophenyl)-5-(1,3,4-oxadiazol-2-yl)-pyridine-3-carboxylic acid of melting point 187°–190° C. Analysis:

| $C_{16}H_{12}N_3O_3Cl_2$ (molecular weight 365.3) | | | | | | | | | | |
|---|---|---|---|---|---|---|---|---|---|---|
| Calculated: | C: | 52.60 | H: | 3.31 | N: | 11.50 | O: | 13.14 | Cl: | 19.44 |
| Found: | | 52.4 | | 3.2 | | 11.3 | | 13.4 | | 19.5 |

EXAMPLE 3

1,4-Dihydro-2,6-dimethyl-3-(1,3,4-oxadiazol-2-yl)-4-(2-chlorophenyl)-pyridine 11 g of 1,4-dihydro-2,6-dimethyl-4-(2-dichlorophenyl)-5-(1,3,4-oxadiazol-2-yl)-pyridine-3-carboxylic acid, prepared in accordance with Example 1, are heated at 180° C. in 50 ml of diethylene glycol for 10 minutes. The mixture is then cooled to room temperature, 250 ml of water are added, the mixture is extracted by shaking with four times 100 ml of ethyl acetate, and the organic phase is dried over sodium sulphate and concentrated. The residue from evaporation is recrystallised from ethyl acetate with the addition of active charcoal. This gives 5.5 g (corresponding to 57.7% of theory) of 1,4-dihydro-2,6-dimethyl-3-(1,3,4-oxadiazol-2-yl)-4-(2-chlorophenyl)-pyridine of melting point 192°–194° C.

| Analysis: $C_{15}H_{13}N_3OCl$ (molecular weight 286.79) | | | | | | | | | | |
|---|---|---|---|---|---|---|---|---|---|---|
| Calculated: | C: | 62.82 | H: | 4.57 | N: | 14.65 | O: | 5.58 | Cl: | 12.38 |
| Found: | | 62.7 | | 4.3 | | 14.7 | | 5.6 | | 12.5 |

EXAMPLE 4

1,4-Dihydro-2,6-dimethyl-3-(1,3,4-oxadiazol-2-yl)-4-(2,3-dichlorophenyl)-pyridine 20 g of 1,4-dihydro-2,6-dimethyl-4-(2,3-dichlorophenyl)-5-(1,3,4-oxadiazol-2-yl)-pyridine-3-carboxylic acid in 100 ml of diethylene glycol are heated at 180° C. for 10 minutes. The mixture is then cooled to room temperature, 500 ml of water are added and the mixture is extracted by shaking with four times 200 ml of ethyl acetate. The organic phase is dried over sodium sulphate and concentrated and the residue is recrystallised from ethyl acetate with the addition of active charcoal. This gives 12.2 g (corresponding to 61% of theory) of 1,4-dihydro-2,6-dimethyl-3-(1,3,4-oxadiazol-2-yl)-4-(2,3-dichlorophenyl)-pyridine, melting point 235° C. with decomposition.

| Analysis: $C_{15}H_{12}N_3OCl_2$ (molecular weight 321.28) | | | | | | | | | | |
|---|---|---|---|---|---|---|---|---|---|---|
| Calculated: | C: | 56.08 | H: | 3.76 | N: | 13.08 | O: | 4.98 | Cl: | 22.10 |
| Found: | | 56.1 | | 3.6 | | 13.0 | | 5.1 | | 22.1 |

EXAMPLES 5 to 30

In analogy to examples 1 to 4 the following compounds are prepared:

1,4-dihydro-2,6-dimethyl-4-(3-chlorophenyl)-5-(1,3,4-oxadiazol-2-yl)-pyridine-3-carboxylic acid, melting point: 182°–184° C.; 1,4-dihydro-2,6-dimethyl-4-(3-nitrophenyl)-5-(3-methyl-1,2,4-oxadiazol-5-yl)-pyridine-3-carboxylic acid, melting point: 209°–211° C.;

1,4-dihydro-2,6-dimethyl-4-(2-nitrophenyl)-5-(3-ethyl-1,2,4-oxadiazol-5-yl)-pyridine-3-carboxylic acid, melting point: 205° C.;

1,4-dihydro-2,6-dimethyl-4-(2-trifluoromethylphenyl)-5-(1,3,4-oxadiazol-2-yl)-pyridine-3-carboxylic acid, melting point: 198° C.;

1,4-dihydro-2,6-dimethyl-4-(3-trifluoromethylphenyl)-5-(2-methyl-1,3,4-oxadiazol-5-yl)-pyridine-3-carboxylic acid, melting point: 180°–183° C.

1,4-dihydro-2,6-dimethyl-4-(2-methoxyphenyl)-5-(5-benzyl-1,3,4-oxadiazol-2-yl)-pyridine-3-carboxylic acid, melting point: 231°–233° C.;

1,4-dihydro-2,6-dimethyl-4-(3-cyanophenyl)-5-(4-methyl-5-ethoxycarbonyl-thiazol-2-yl)-pyridine-3-carboxylic acid, melting point: 242°–245° C.;

1,4-dihydro-2,6-dimethyl-4-(pyrid-2-yl)-5-(5-methoxymethyl-1,2,4-oxadiazol-3-yl)-pyridine-3-carboxylic acid, melting point: 198°–201° C.;

1,4-dihydro-2,6-dimethyl-4-(2,3-dichlorophenyl)-5-(3-benzyl-1,2,4-oxadiazol-5-yl)-pyridine-3-carboxylic acid, melting point: 212° C.;

1,4-dihydro-2,6-dimethyl-4-(2-thienyl)-5-(5-isopropylthio-1,3,4-oxadiazol-2-yl)-pyridine-3-carboxylic acid, melting point: 271°–218° C.;

1,4-dihydro-2,6-dimethyl-4-(2-methylphenyl)-5-(5-cyclohexyl-1,2,4-oxadiazol-3-yl)-pyridine-3-carboxylic acid, melting point: 218° C.;

1,4-dihydro-2,6-dimethyl-4-(2-benzyloxyphenyl)-5-(2-ethyl-1,3,4-oxadiazol-5-yl)-pyridine-3-carboxylic acid, melting point: 193°–194° C.;

1,4-dihydro-2,6-dimethyl-4-(3-methoxyphenyl)-5-(3-methyl-1,2,4-thiadiazol-5-yl)-pyridine-3-carboxylic acid, melting point: 184°–186° C.;

1,4-dihydro-2,6-dimethyl-4-(3-chlorophenyl)-5-(1,3,4-oxadiazol-2-yl)-pyridine, melting point: 182° C.;

1,4-dihydro-2,6-dimethyl-4-(3-nitrophenyl)-5-(3-methyl-1,2,4-oxadiazol-5-yl)-pyridine, melting point: 176°–178° C.;

1,4-dihydro-2,6-dimethyl-4-(2-nitrophenyl)-5-(3-ethyl-1,2,4-oxadiazol-5-yl)-pyridine, melting point: 209°–211° C.;

1,4-dihydro-2,6-dimethyl-4-(2-trifluoromethylphenyl)-5-(1,3,4-oxadiazol-2-yl)-pyridine, melting point: 199°–202° C.;

1,4-dihydro-2,6-dimethyl-4-(3-trifluoromethylphenyl)-5-(2-methyl-1,3,4-oxadiazol-5-yl)-pyridine, melting point: 191°–192° C.;

1,4-dihydro-2,6-dimethyl-4-(2-methoxyphenyl)-5-(5-benzyl-1,3,4-oxadiazol-2-yl)-pyridine, melting point: 205° C.;

1,4-dihydro-2,6-dimethyl-4-(3-cyanophenyl)-5-(4-methyl-5-ethoxycarbonyl-thiazol-2-yl)-pyridine, melting point: 198°–201° C.;

1,4-dihydro-2,6-dimethyl-4-(pyrid-2-yl)-5-(5-methoxymethyl-1,2,4-oxadiazol-3-yl)-pyridine, melting point: 188°–189° C.;

1,4-dihydro-2,6-dimethyl-4-(2,3-dichlorophenyl)-5-(3-benzyl-1,2,4-oxadiazol-5-yl)-pyridine, melting point: 201°–203° C.;

1,4-dihydro-2,6-dimethyl-4-(2-thienyl)-5-(5-isopropylthio-1,3,4-oxadiazol-2-yl)-pyridine, melting point: 192° C.;

1,4-dihydro-2,6-dimethyl-4-(2-methylphenyl)-5-(5-cyclohexyl-1,2,4-oxadiazol-3-yl)-pyridine, melting point: 221° C.;

1,4-dihydro-2,6-dimethyl-4-(2-benzyloxyphenyl)-5-(2-ethyl-1,3,4-oxadiazol-5-yl)-pyridine, melting point: 202°–205° C.;

1,4-dihydro-2,6-dimethyl-4-(3-methoxyphenyl)-5-(3-methyl-1,2,4-thiadiazol-5-yl)-pyridine, melting point: 196°–198° C.

The following examples A to C relate to pharmaceutical preparations:

| Example A: Coated Tablets | |
|---|---|
| active substance | 10 mg |
| lactose | 80 mg |
| cornstarch | 110 mg |
| sec. calcium phosphate | 40 mg |
| soluble starch | 3 mg |
| magnesium stearate | 3 mg |
| colloidal silicic acid | 4 mg |
| | 250 mg |
| Example B: Tablets | |
| active substance | 20 mg |
| lactose | 60 mg |
| cornstarch | 35 mg |
| soluble starch | 4 mg |
| magnesium stearate | 1 mg |
| | 120 mg |
| Example C: Capsules | |
| active substance | 15 mg |
| cornstarch | 185 mg |
| | 200 mg |

We claim:

1. A 1,4-dihydropyridine of the formula

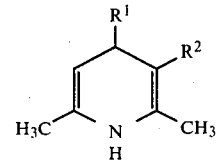

wherein $R^1$ is a phenyl radical unsubstituted or optionally substituted with one or two identical or different substituents selected from the group consisting of alkyl having 1 to 4 carbon atoms, alkoxy having 1 to 4 carbon atoms, halogen, trifluoro-methyl, nitro, cyano and benzyloxy groups, $R^2$ is a radical selected from the group consisting of 1,2,4-oxadiazole, 1,3,4-oxadiazole, 1,2,4-thiadiazole and 1,3,4-thiadiazole radicals which are either unsubstituted or substituted with a radical selected from the group consisting of alkyl having 1 to 4 carbon atoms, alkoxy having 1 to 4 carbon atoms, alkylthio having 1 to 4 carbon atoms, aralkyl having 7 to 9 carbon atoms, alkoxyalkyl having a total of 2 to 5 carbon atoms, cycloalkyl having 5 or 6 carbon atoms, amino-carbonylmethylthio, methoxy carbonyl, ethoxycarbonyl and phenyl, and salts thereof with pharmacologically acceptable acids.

2. A 1,4-dihydropyridine according to claim 1 wherein $R^1$ denotes phenyl which is unsubstituted or which contains one or two identical or different substituents selected from the group consisting of halogen, methyl, methoxy, nitro, trifluoromethyl, cyano and benzyloxy.

3. A 1,4-dihydropyridine according to claim 1 wherein $R^2$ denotes a 1,2,4-oxadiazolyl or or 1,3,4-oxadiazolyl radical which contains a substituent selected from the group consisting of methyl, ethyl, isropyl and benzyl.

4. 1,4-Dihydro-2,6-dimethyl-3-(1,3,4-oxadiazol-2-yl)-4-(2-chlorophenyl)-pyridine.

5. 1,4-Dihydro-2,6-dimethyl-3-(3-ethyl-1,2,4-oxadiazol-5-yl)-4-(2-trifluoromethylphenyl)-pyridine.

6. 1,4-Dihydro-2,6-dimethyl-3-(1,3,4-oxadiazol-2-yl)-4-(2,3-dichlorophenyl)-pyridine.

7. A pharmaceutical formulation which exhibits a pronounced calcium-agonistic action when administered to a host, having as active component from about 0.5 to 90% by weight of a compound of one of the claims 2, 3, 4, 5, 6 or 1, together with a pharmaceutically-acceptable vehicle and, optionally, a pharmaceutically-acceptable additive.

8. A method for treating angina pectoris, high blood pressure or disturbances of cerebral or peripheral blood flow which comprises administering an effective amount of a pharmaceutical formulation of claim 7, to a host, which is subject to or afflicted with one or more of these conditions.

* * * * *